United States Patent [19]

Böhner et al.

[11] 4,243,410
[45] Jan. 6, 1981

[54] HERBICIDALLY ACTIVE α-(4-PHENOXYPHENOXY)PROPIONIC ACID ALKOXYALKYL AMIDES, HERBICIDAL COMPOSITIONS CONTAINING THEM AND THEIR USE

[75] Inventors: Beat Böhner, Binningen; Otto Rohr, Therwil, both of Switzerland

[73] Assignee: Ciba-Geigy Corporation, Ardsley, N.Y.

[21] Appl. No.: 1,515

[22] Filed: Jan. 8, 1979

[30] Foreign Application Priority Data

Jan. 10, 1978 [CH] Switzerland ............... 223782/78

[51] Int. Cl.³ ............... A01N 37/18; C07C 103/178
[52] U.S. Cl. ............... 71/118; 564/171; 71/88
[58] Field of Search ......... 71/118; 260/559 B, 559 D

[56] References Cited

U.S. PATENT DOCUMENTS

| | | | |
|---|---|---|---|
| 3,937,730 | 2/1976 | Vogel et al. | 71/118 |
| 4,143,070 | 3/1979 | Walker | 71/118 |

FOREIGN PATENT DOCUMENTS

| | | | |
|---|---|---|---|
| 2433067 | 1/1976 | Fed. Rep. of Germany | 71/118 |
| 2531643 | 1/1976 | Fed. Rep. of Germany | 71/118 |

*Primary Examiner*—Glennon H. Hollrah
*Attorney, Agent, or Firm*—Harry Falber

[57] ABSTRACT

The present invention relates to novel herbicidally active 4-(p-trifluoromethylphenoxy)-α-phenoxypropionic acid alkoxyalkyl amides, processes for their manufacture and also herbicidal compositions which contain them. The preferred utility of the novel compounds is the selective control of monocotyledonous weeds.

The novel compounds have the general formula I

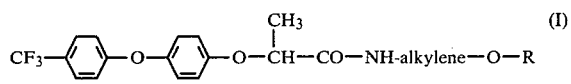

wherein "alkylene" represents a straight or branched saturated hydrocarbon chain of 1 to 4 carbon atoms and R represents an alkyl radical of 1 to 4 carbon atoms.

The novel compounds are obtained by reacting a halide or lower alkyl ester of 4-(p-trifluoromethylphenoxy)-α-phenoxypropionic acid with an alkoxyalkyl amine

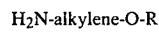

or by reacting a hydroxydiphenyl ether

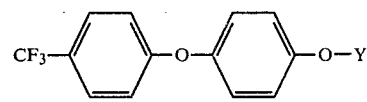

wherein Y is hydrogen or a cation, with an α-halopropionic acid alkoxyalkyl amide of the formula

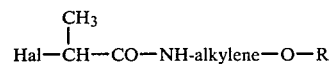

in the presence of an acid acceptor.

Preferred compounds of the formula I are an N-(2-methoxy)-ethylamide and N-(3-methoxy)-propyl-(2)-amide.

8 Claims, No Drawings

HERBICIDALLY ACTIVE α-(4-PHENOXYPHENOXY)PROPIONIC ACID ALKOXYALKYL AMIDES, HERBICIDAL COMPOSITIONS CONTAINING THEM AND THEIR USE

The present invention relates to novel herbicidally active, trifluoromethylated α-(phenoxyphenoxy)-propionic acid alkoxyalkyl amides, processes for their manufacture, compositions which contain these novel compounds as active components, and a method of selectively controlling weeds in crops of cultivated plants which comprises the use of the novel compounds and compositions containing them.

In recent years there has appeared an extensive range of patent literature relating to herbicidally active, variously substituted diphenyl ethers, including phenoxy-phenoxyalkanecarboxylic acids, their salts, esters and other derivatives.

Various amides of 4-(p-trifluoromethylphenoxy)-α-phenoxypropionic acid constitute the closest prior art. Amides of this acid which do not contain functional groups in the amide moiety, such as the amide and methylamide, have been published in German Offenlegungsschrift 2,433,067, 2,531,643 and 2,639,796. German Offenlegungsschrift 2,531,643 and Japanese published patent specification 52-130912 disclose amides of this acid containing ether groups (also cyclic groups) in the amide side chain, such as the N-methoxyamide and the morpholide.

The novel 4-(p-trifluoromethylphenoxy)-α-phenoxypropionic acid alkoxyalkyl amides of the present invention have the formula I

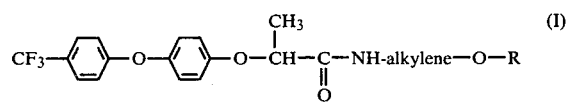

wherein "alkylene" represents a straight or branched saturated hydrocarbon chain of 1 to 4 carbon atoms, and R represents an alkyl radical of 1 to 4 carbon atoms.

The alkyl radical can be straight-chain or branched and thus embraces methyl, ethyl, propyl, isopropyl and the four possible butyl radicals.

In addition to methylene (—CH$_2$—), particular mention may be made of the following as possible alkylene chains:

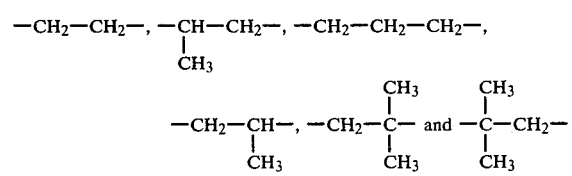

The active compounds of the formula I and the herbicidal compositions containing them as active component are especially useful for controlling grass-like monocotyledonous weeds, and in this respect are clearly superior to the amide compounds referred to above, especially in post-emergent application.

The known compounds do not exhibit a sufficient herbicidal activity towards weeds which are difficult to control, especially in low rates of concentration, or else they also damage the cultivated plants when used in the rates of application necessary for controlling the weeds.

Surprisingly, the active compounds of the formula I of the present invention exhibit a better herbicidal action than the products previously referred to. Moreover, the compounds of the present invention are very well tolerated by cultivated plants, for example soya, sugar beet, cotton etc. Accordingly, it is the object of the present invention to provide new active compounds (active substances) belonging to the series of the α-(phenoxyphenoxy)-propionic acid derivatives, which are superior to known compounds of similar structure in their herbicidal action against monocotyledonous weeds which are difficult to control, and which are tolerated by important cultivated plants, that is to say, compounds which enlarge the stock of technical knowledge.

The compounds of the formula I can be obtained by methods which are in themselves known.

One of these methods consists in reacting a corresponding 4-trifluoromethylphenoxy-α-phenoxypropionic acid halide of the formula II

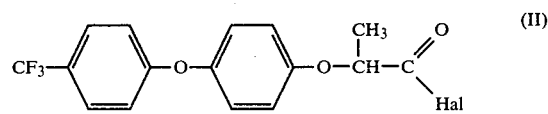

wherein Hal represents a halogen atom, in particular a chlorine atom, in the presence of a basic acid acceptor, with an alkoxyalkylamine of the formula III

wherein "alkylene" and R are as defined for formula I.

In a variant of this process, it is possible to react, instead of the acid halide of the formula II, a lower alkyl ester of this acid, in particular the methyl ester, with the amine of the formula III, under conditions which effect elimination of the alkanol (methanol) from which the ester is derived.

This aminolysis of relatively easily saponifiable carboxylic acid esters is a generally applicable method of obtaining carboxamides and can be carried out, for example, by dispersing and shaking the carboxylic acid ester in aqueous amine solutions at low temperature.

Another process consists in reacting the hydroxydiphenyl ether, or a salt thereof, of the formula IV

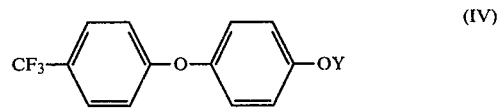

wherein Y represents hydrogen or the cation of an alkali metal or the equivalent of an alkaline earth metal cation, with an α-halopropionic acid alkoxyalkyl amide of the formula V

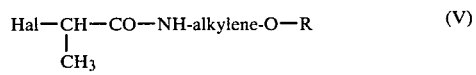

in the presence of an acid acceptor (base).

The reactions are preferably carried out in a solvent which is inert to the reactants. Suitable solvents are those of the most widely different classes, such as aliphatic and aromatic, unsubstituted or chlorinated hydrocarbons, for example ethylene chloride etc., and also polar organic solvents, such as alcohols, ethers, ketones, amides, stable esters, for example methyl ethyl ketone, dimethoxy ethane, dimethyl formamide, dimethyl sulfoxide, tetrahydrofurane etc.

Suitable basic acid acceptors for the reaction with the halogen compounds of the formula II and V can be aqueous alkali metal hydroxides, such as KOH and NaOH, as well as further conventional bases, such as carbonates ($K_2CO_3$, $NaHCO_3$), alcoholates ($NaOCH_3$ and potassium tertbutylate), and organic bases, such as triethylamine etc.

Most of the starting materials of the formulae II to V are known. If certain amines falling under the formula III should be new, they can be readily obtained by the methods ordinarily employed for obtaining the known ones. Novel α-halopropionamides of the formula V are obtained from the corresponding propionic acid halides and amines of the formula III.

The following Example illustrates the manufacture of an active substance of the formula I. Further active substances obtained in analogous manner or by another of the methods described, are listed in the subsequent table.

EXAMPLE

While cooling with ice, 17.2 g (0.05 mole) of α-[4-(p-trifluoromethylphenoxy)-phenoxy]-propionyl chloride are added dropwise to a mixture of 4.1 g (0.055 mole) of 2-methoxyethylamine, 7.5 ml (0.055 mole) of triethylamine and 50 ml of methylene chloride, and the temperature is allowed to rise to 20° C. The reaction mixture is stirred for 2 hours, then concentrated. The residue is filtered in ether over a small column of silica gel. Concentration of the filtrate affords 14.9 g (77.6%) of α-[4-(p-trifluoromethylphenoxy)-phenoxy]-propionic acid (2-methoxy)-ethylamide with a melting point of 73°-75° C.

The following compounds of the formula I were also prepared in alalogous manner:

| Compound | alkylene—O—R | m.p. °C. |
| --- | --- | --- |
| 1 | —CH$_2$—CH$_2$—O—CH$_3$ | 73°-75° |
| 2 | —CH$_2$—CH$_2$—O—C$_2$H$_5$ | 72°-73° |
| 3 | —CH$_2$—CH$_2$—O—C$_3$H$_7$(n) | 70°-72° |
| 4 | —CH—CH$_2$—O—CH$_3$<br>    |<br>   CH$_3$ | 62°-65° |
| 5 | —CH$_2$—CH$_2$—CH$_2$—OCH$_3$ | 69°-70° |
| 6 | —CH$_2$—CH$_2$—CH$_2$—O—C$_2$H$_5$ | 60°-61° |
| 7 | —CH$_2$—CH$_2$—CH$_2$—O—C$_3$H$_7$(i) | 60°-61° |
| 8 | —CH$_2$—OCH$_3$ | |
| 9 | —CH$_2$—O—C$_2$H$_5$ | |
| 10 | —CH$_2$—CH—O—CH$_3$<br>       |<br>      CH$_3$ | |
| 11 |    CH$_3$<br>   |<br>—CH—CH$_2$—O—CH$_3$<br>   |<br>   CH$_3$ | |
| 12 |      CH$_3$<br>     |<br>—CH$_2$—C—O—CH$_3$<br>     |<br>     CH$_3$ | |

The invention also relates to herbicidal compositions which contain a novel active substance of the formula I, and to a pre-emergent, especially post-emergent method of controlling weeds, in particular monocotyledonous grasslike weeds.

The compositions of the present invention can be in the conventional formulations.

The compositions of the present invention are obtained in known manner by intimately mixing and grinding active substances of the formula I with suitable carriers, with or without the addition of dispersants or solvents which are inert to the active substances. The active substances can be processed to the following formulations:

solid formulations: dusts, tracking powders, granules (coated granules, impregnated granules and homogeneous granules);

active substance concentrates which are dispersible in water: wettable powders, pastes, emulsions, emulsifiable concentrates;

liquid formulations: solutions.

Solid forms (dusts, tracking powders), are obtained by mixing the active substances with solid carriers. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulfates, magnesium oxide, ground synthetic materials, fertilisers, for example ammonium sulfate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

Granulates can be prepared by dissolving the active substances in an organic solvent and applying the resultant solution to a granulated material, for example attapulgite, $SiO_2$, granicalcium, bentonite etc., and then evaporating the solvent.

Polymer granulates can also be prepared by impregnating a finished, porous polymer granulate (urea/formaldehyde polymers, polyacrylonitrile, polyester and others), which has a specific surface area and a favourable predetermined adsorption/desorption ratio, with the active substances, for example in the form of their solutions (in a low boiling solvent) and removing the solvent. Polymer granulates of this kind in the form of microgranules having a bulk density of 300 g/liter to 600 g/liter can also be produced with the aid of atomisers. The dusting can be carried out from aircraft over extensive treatment areas.

It is also possible to obtain granulates by compacting the carrier with the active substance and carriers and subsequently comminuting the product.

To these mixtures can also be added additives which stabilize the active substance and/or nonionics, anionics and cationics, which, for example, improve the adhesion of the active ingredients on plants or parts of plants (adhesives and sticking agents) and/or ensure a better wettability (wetting agents) and dispersibility (dispersing agents). Examples of suitable substances are: olein/-chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl moiety, ligninsulfonic acids, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances and anti-foam agents and, if appropriate, solvents.

Wettable powders and pastes are obtained by mixing and grinding the active substances with dispersing agents and pulverulent carriers in suitable devices until homogeneity is attained. Suitable carriers are, for example, those already mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehyde, as well as alkali metal, ammonium and alkaline earth metal salts of ligninsulfonic acid, in addition, alkylarysulfonates, alkali metal and alkaline earth metal salts of dibutynaphthalene-sulfonic acid, fatty alcohol sulfates, such as salts of sulfated hexadecanols, heptadecanols, octadecanols, and salts of sulfated fatty alcohol glycol ethers, the sodium salt of oleyl methyl tauride, ditertiary ethylene glycols, dialkyldilaurylammonium chloride and fatty acid alkali metal and alkaline earth metal salts.

Suitable anti-foam agents are silicones. The active substances are so mixed, ground sieved and strained with the additives mentioned above that, in wettable powders, the solid particle size of 0.02 to 0.04 mm and in pastes, of 0.03 mm, is not exceeded. Emulsifiable concentrates and pastes are manufactured by using dispersing agents, such as those cited previously above, organic solvents, and water. Examples of suitable solvents are: alcohols, xylenes, toluene, dimethyl sulfoxide, N,N-dialkylated amides and trialkylamines. The solvents must be practically odourless, not phytotoxic, inert to the active substances, and not readily combustible.

Furthermore, the compositions of the invention can be applied in the form of solutions. For this purpose the active substances or several active substances of the general formula I are dissolved in suitable organic solvents, mixtures of solvents or in water. Aliphatic and aromatic hydrocarbons, chlorinated derivatives thereof, alkylnaphthalenes and mineral oils, singly or in admixture, can be used as organic solvents.

The above described compositions contain between 0.1 and 95%, preferably between 1 and 80%, of active substance. Formulations can be diluted to a concentration as low as 0.001%. The rates of application are normally from 0.1 to 10 kg of active substance per hectare, preferably 0.25 to 5 kg per hectare. The active substances can be formulated for example as follows (parts are by weight):

Wettable powders

The following constituents are used to formulate (a) a 50%, (b) a 25% and (c) a 10% wettable powder:

(a)
50 parts of 4-(p-trifluoromethyl-phenoxy)-α-phenoxypropionic acid (3-methoxy)-propyl-(2)-amide,
5 parts of sodium dibutylnaphthylsulfonate,
3 parts of naphthalenesulfonic acid/phenolsulfonic acid/formaldehyde concentrate (3:2:1),
20 parts of kaolin,
22 parts of Champagne chalk;

(b)
25 parts of 4-(p-trifluoromethyl-phenoxy)-α-phenoxypropionic acid (2-methoxy)-ethylamide,
5 parts of sodium oleylmethyltauride,
2.5 parts of naphthalenesulfonic acid/formaldehyde condensate
0.5 part of carboxymethyl cellulose,
5 parts of neutral potassium aluminium silicate,
62 parts of kaolin;

(c)
10 parts of one of the above active substances,
3 parts of a mixture of the sodium salts of saturated fatty alcohol sulphates,
5 parts of naphthalenesulfonic acid/formaldehyde condensate,
82 parts of kaolin.

The indicated active substance is applied to the corresponding carriers (kaolin and chalk) and then these are mixed and ground, to yield wettable powders of excellent wettability and suspension powder. By diluting these wettable powders with water it is possible to obtain suspensions of the desired concentration of active substance. Such suspensions are used for controlling weeds and grasslike weeds in crops of cultivated plants.

Paste

The following substances are used to formulate a 45% paste:
45 parts of 4-(p-trifluoromethyl-phenoxy)-α-phenoxypropionic acid (3-ethoxy)-propyl-(1)-amide,
5 parts of sodium aluminium silicate,
14 parts of acetyl polyglycol ether with 8 moles of the ethylene oxide,
1 part of oleyl polyglycol ether with 5 moles of the ethylene oxide,
2 parts of spindle oil,
10 parts of polyethylene glycol,
23 parts of water.

The active substance is homogeneously mixed with the adjuvants in appropriate devices and ground, yielding a paste from which, by dilution with water, it is possible to obtain suspensions of the desired concentration of active substance.

Emulsifiable Concentrate

The following ingredients are mixed to formulate a 25% emulsifiable concentrate:
25 parts of 4-(p-trifluoromethyl-phenoxy)-α-phenoxypropionic acid (3-ethoxy)-propyl-(1)-amide,
10 parts of a mixture on nonylphenolpolyoxy-ethylene and calcium dodecylbenzenesulfonate,
55 parts of Xylene
10 parts of cyclohexanone.

This concentrate can be diluted with water to produce emulsions of suitable concentrations. Instead of the active substance respectively indicated in the above formulation Examples, it is also possible to use another of the compounds embraced by the formula I.

Compositions of the invention which contain, as active component, a compound of the formula I, are particularly suitable for the selective pre-emergent, and, in particular, post-emergent, control of monocotyledonous weeds in crops of cultivated plants, for example soya beans, cotton, sugar beet etc.

The following test methods were employed to establish the usefulness of the compounds of the formula I as pre-emergent and post-emergent herbicides.

Pre-emergent herbicidal action

In a greenhouse, immediately after sowing the test plants in seed dishes, the surface of the soil is treated with an aqueous dispersion of the active substances, obtained from a 25% emulsifiable concentrate or from a 25% wettable powder with active substances which, on account of their insufficient solubility, cannot be formulated to an emulsifiable concentrate. Four different concentration series were used, corresponding to 4, 2, 1 and 0.5 kg of active substance per hectare respectively. The seed dishes are kept in the greenhouse at 22°–25° C. and 50–70% relative humidity. The test is evaluated 3 weeks later according to the following rating:

1 = plants have not germinated or are totally withered
2–3 = very strong action
4–6 = average action
7–8 = slight action
9 = no action (as untreated control)

The following test plants were used:

| | |
|---|---|
| hordeum (barley) | setaria italica |
| triticum (wheat) | echinochloa crus galli |
| zea (Mais) | beta vulgaris |
| sorghum hybr. (millet) | sida spinosa |
| oryza (rice) | sesbania exaltata |
| glycine (soya) | amaranthus retroflexus |
| gossypium (cotton) | sinapis alba |
| avena fatua | ipomoea purpurea |
| lolium perenne | galium aparine |
| alopecurus myosuroides | pastinaca sativa |
| bromus tectorum | rumex sp. |
| cyperus esculentus | chrysanthemum leucum. |
| rottboellia exaltata | abutilon sp. |
| digitaria sanguinalis | solanum nigrum |

Post-emergent herbicidal action (Contact herbicide)

A large number (at least 7) of weeds and cultivated plants, both mono- and dicotyledonous, were sprayed after emergence in the 4- to 6-leaf stage with an aqueous active substance emulsion in rates of 0.06, 0.125, 0.25 and 0.5 kg of active substance per hectare and kept at 24°–26° C. and 45–60% relative humidity. The test was evaluated, as in the preemergent test, 15 days after treatment in accordance with the same rating.

Soya, cotton and sugar beet were used in this test as cultivated plants. As monocotyledonous weeds, eight plants were elected from the list indicated in the preemergence test.

The following prior art compounds were used as known comparison substances:

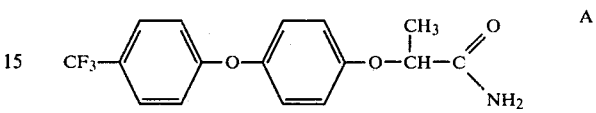

German Offenlegungsschrift 2 639 796

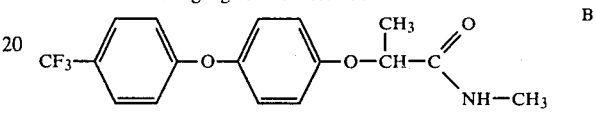

German Offenlegungsschrift 2 433 067

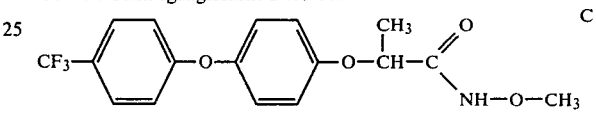

Japanese publication 52-130912

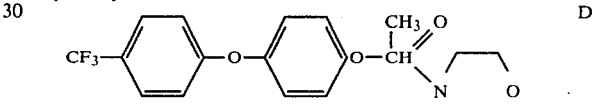

German Offenlegungsschrift 2 531 643

The tested active substances of the invention correspond to the numbering in the Table following the Example.

Results

| Compound | rate of application in g/ha | Avena | Lolium | Alopecurus | Bromus | Rottboellia | Digitaria | Setaria | Echinochloa | soya | cotton | sugar beet |
|---|---|---|---|---|---|---|---|---|---|---|---|---|
| A | 500 | 9 | 6 | 5 | 7 | 9 | 2 | 2 | 1 | 9 | 9 | 9 |
|   | 250 | 9 | 8 | 6 | 8 | 9 | 3 | 2 | 1 | 9 | 9 | 9 |
|   | 125 | 9 | 9 | 6 | 9 | 9 | 4 | 2 | 2 | 9 | 9 | 9 |
|   | 60  | 9 | 9 | 6 | 9 | 9 | 5 | 2 | 3 | 9 | 9 | 9 |
| B | 500 | 3 | 2 | 3 | 9 | 4 | 1 | 1 | 1 | 9 | 9 | 9 |
|   | 250 | 4 | 4 | 3 | 9 | 7 | 2 | 1 | 1 | 9 | 9 | 9 |
|   | 125 | 7 | 8 | 9 | 9 | 9 | 2 | 1 | 2 | 9 | 9 | 9 |
|   | 60  | 9 | 9 | 9 | 9 | 9 | 3 | 4 | 3 | 9 | 9 | 9 |
| C | 500 | 7 | 6 | 3 | 6 | 3 | 1 | 1 | 1 | 9 | 9 | 9 |
|   | 250 | 7 | 7 | 4 | 9 | 7 | 1 | 1 | 1 | 9 | 9 | 9 |
|   | 125 | 9 | 9 | 6 | 9 | 8 | 3 | 2 | 1 | 9 | 9 | 9 |
|   | 60  | 9 | 9 | 7 | 9 | 9 | 3 | 2 | 4 | 9 | 9 | 9 |
| D | 500 | 9 | 9 | 7 | 9 | 9 | 5 | 1 | 9 | 9 | 9 | 9 |
|   | 250 | 9 | 9 | 7 | 9 | 9 | 6 | 2 | 9 | 9 | 9 | 9 |
|   | 125 | 9 | 9 | 8 | 9 | 9 | 9 | 3 | 9 | 9 | 9 | 9 |
|   | 60  | 9 | 9 | 9 | 9 | 9 | 9 | 4 | 9 | 9 | 9 | 9 |
| 1 | 500 | 1 | 1 | 1 | 1 | 1 | 1 | 1 | 1 | 9 | 7 | 9 |
|   | 250 | 1 | 2 | 2 | 2 | 1 | 1 | 1 | 1 | 9 | 8 | 9 |
|   | 125 | 3 | 2 | 2 | 2 | 1 | 1 | 1 | 1 | 9 | 9 | 9 |
|   | 60  | 4 | 3 | 3 | 4 | 1 | 1 | 1 | 1 | 9 | 9 | 9 |
| 2 | 500 | 1 | 1 | 1 | 1 | 1 | 1 | 1 | 1 | 9 | 7 | 9 |
|   | 250 | 1 | 1 | 1 | 2 | 1 | 1 | 1 | 1 | 9 | 7 | 9 |
|   | 125 | 2 | 2 | 2 | 2 | 1 | 1 | 1 | 1 | 9 | 9 | 9 |
|   | 60  | 7 | 6 | 3 | 4 | 1 | 1 | 1 | 1 | 9 | 9 | 9 |
| 4 | 500 | 1 | 1 | 1 | 1 | 1 | 1 | 1 | 1 | 9 | 8 | 9 |
|   | 250 | 1 | 1 | 2 | 2 | 1 | 1 | 1 | 1 | 9 | 9 | 9 |
|   | 125 | 3 | 2 | 2 | 3 | 1 | 1 | 1 | 1 | 9 | 9 | 9 |

-continued

| Compound | rate of application in g/ha | Avena | Lolium | Alopecurus | Bromus | Rottboellia | Digitaria | Setaria | Echinochloa | soya | cotton | sugar beet |
|---|---|---|---|---|---|---|---|---|---|---|---|---|
|   | 60  | 6 | 2 | 3 | 4 | 1 | 1 | 1 | 1 | 9 | 9 | 9 |
| 5 | 500 | 1 | 1 | 1 | 2 | 1 | 1 | 1 | 1 | 9 | 9 | 9 |
|   | 250 | 1 | 2 | 2 | 2 | 1 | 1 | 1 | 1 | 9 | 9 | 9 |
|   | 125 | 4 | 3 | 2 | 3 | 1 | 1 | 1 | 1 | 9 | 9 | 9 |
|   | 60  | 7 | 4 | 3 | 6 | 2 | 1 | 1 | 1 | 9 | 9 | 9 |
| 6 | 500 | 2 | 2 | 3 | 3 | 1 | 1 | 1 | 1 | 9 | 9 | 9 |
|   | 250 | 6 | 3 | 6 | 4 | 1 | 1 | 1 | 1 | 9 | 9 | 9 |
|   | 125 | 8 | 5 | 6 | 9 | 1 | 1 | 1 | 1 | 9 | 9 | 9 |
|   | 60  | 9 | 9 | 6 | 9 | 5 | 1 | 1 | 2 | 9 | 9 | 9 |

Good results were also obtained in the pre-emergent test. The best results were obtained with compound 4.

What is claimed is:

1. A herbicidally active 4-(p-trifluoromethylphenoxy)-α-phenoxypropionic acid alkoxyalkyl amide of the formula I

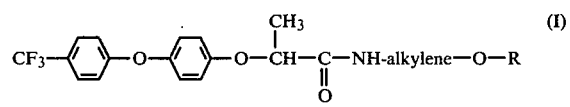

wherein "alkylene" represents a straight or branched saturated hydrocarbon chain of 1 to 4 carbon atoms and R represents an alkyl radical of 1 to 4 carbon atoms.

2. A 4-(p-trifluoromethylphenoxy)-α-phenoxypropionic acid alkoxyalkyl amide according to claim 1, wherein "alkylene" in formula I represents the ethylene chain —CH$_2$—CH$_2$— or a straight or branched propylene chain.

3. 4-(p-trifluoromethylphenoxy)-α-phenoxypropionic acid N-(2-methoxy)-ethylamide according to claim 1.

4. 4-(p-trifluoromethylphenoxy)-α-phenoxypropionic acid N-(3-methoxy)-propyl-(2)-amide.

5. A herbicidal composition which contains, as active component, a herbicidally effective amount of a 4-(p-trifluoromethylphenoxy)-α-phenoxypropionic acid alkoxyalkyl amide of the formula I of claim 1, together with a suitable inert carrier therefor.

6. A method of controlling monocotyledonous weeds at a locus, which comprises applying to said locus an effective amount of a 4-(p-trifluoromethylphenoxy)-α-phenoxypropionic acid alkoxyalkyl amide of the formula I of claim 1.

7. A method according to claim 6 of selectively controlling monocotyledonous weeds in crops of cultivated plants.

8. A method according to claim 6 in which the compound applied is 4-(p-trifluoromethylphenoxy)-α-phenoxypropionic acid N-(2-methoxy)-ethylamide.

* * * * *